(12) United States Patent
Tobey

(10) Patent No.: US 8,272,076 B2
(45) Date of Patent: Sep. 25, 2012

(54) COVER FOR AN EYEWEAR STRAP

(75) Inventor: Karen R. Tobey, Wilmette, IL (US)

(73) Assignee: Gogglemate, Inc., Wilmette, IL (US)

( * ) Notice: Subject to any disclaimer, the term of this patent is extended or adjusted under 35 U.S.C. 154(b) by 447 days.

(21) Appl. No.: 12/565,804

(22) Filed: Sep. 24, 2009

(65) Prior Publication Data

US 2010/0071118 A1    Mar. 25, 2010

Related U.S. Application Data

(60) Provisional application No. 61/194,202, filed on Sep. 25, 2008.

(51) Int. Cl.
  *A61F 9/02* (2006.01)
(52) U.S. Cl. ......................................................... 2/452
(58) Field of Classification Search ............... 2/209.13, 2/181.4, 244, 452; 351/156, 157; D16/339, D16/309
  See application file for complete search history.

(56) References Cited

U.S. PATENT DOCUMENTS

| | | | |
|---|---|---|---|
| 2,643,380 A * | 6/1953 | Blair ................................. | 2/460 |
| D294,710 S | 3/1988 | Witzel | |
| D305,901 S | 2/1990 | Witzel | |
| 5,003,640 A | 4/1991 | Pizzacar | |
| 5,087,118 A | 2/1992 | Gill | |
| D330,717 S | 11/1992 | Rupert et al. | |
| 5,287,559 A | 2/1994 | Christiansen et al. | |
| 5,428,844 A | 7/1995 | Dougherty | |
| D361,081 S | 8/1995 | Pardinas | |
| 5,517,695 A | 5/1996 | Murray | |
| 5,595,332 A * | 1/1997 | Freedman ....................... | 224/264 |
| 5,600,855 A * | 2/1997 | Ramirez ......................... | 2/209.13 |
| D387,797 S * | 12/1997 | Alcock et al. ................. | D16/330 |
| 5,857,220 A | 1/1999 | Erny et al. | |
| D411,562 S | 6/1999 | Riley | |
| 6,279,168 B1 * | 8/2001 | Bean ............................ | 2/209.13 |
| 6,322,149 B1 * | 11/2001 | Conforti et al. ............... | 297/482 |
| 6,658,664 B1 * | 12/2003 | Verhoeven ........................ | 2/12 |
| 6,807,680 B2 | 10/2004 | Sloot | |
| D628,230 S * | 11/2010 | Tobey .......................... | D16/339 |
| 7,833,085 B2 * | 11/2010 | Crouch .......................... | 450/86 |
| 2007/0113326 A1 | 5/2007 | Pennell et al. | |

OTHER PUBLICATIONS

International Search Report and Written Opinion for PCT Patent Application No. PCT/US11/66077 dated Apr. 24, 2012, 8 pgs.
Office Action for U.S. Appl. No. 12/973,165 dated Apr. 13, 2012, 6 pgs.

* cited by examiner

*Primary Examiner* — Danny Worrell
(74) *Attorney, Agent, or Firm* — Edwards Wildman Palmer LLP

(57) ABSTRACT

A cover for an eyewear strap is provided. The cover may include a first member, a second member associated with the first member and movable toward and away from the first member, and a fastener connected to the first member and the second member for removably connecting the first member to the second member. The cover may be adapted to receive an eyewear strap between the first and second members when the first and second members are disconnected, and the cover may be securable to the eyewear strap when the first and second members are connected together.

22 Claims, 7 Drawing Sheets

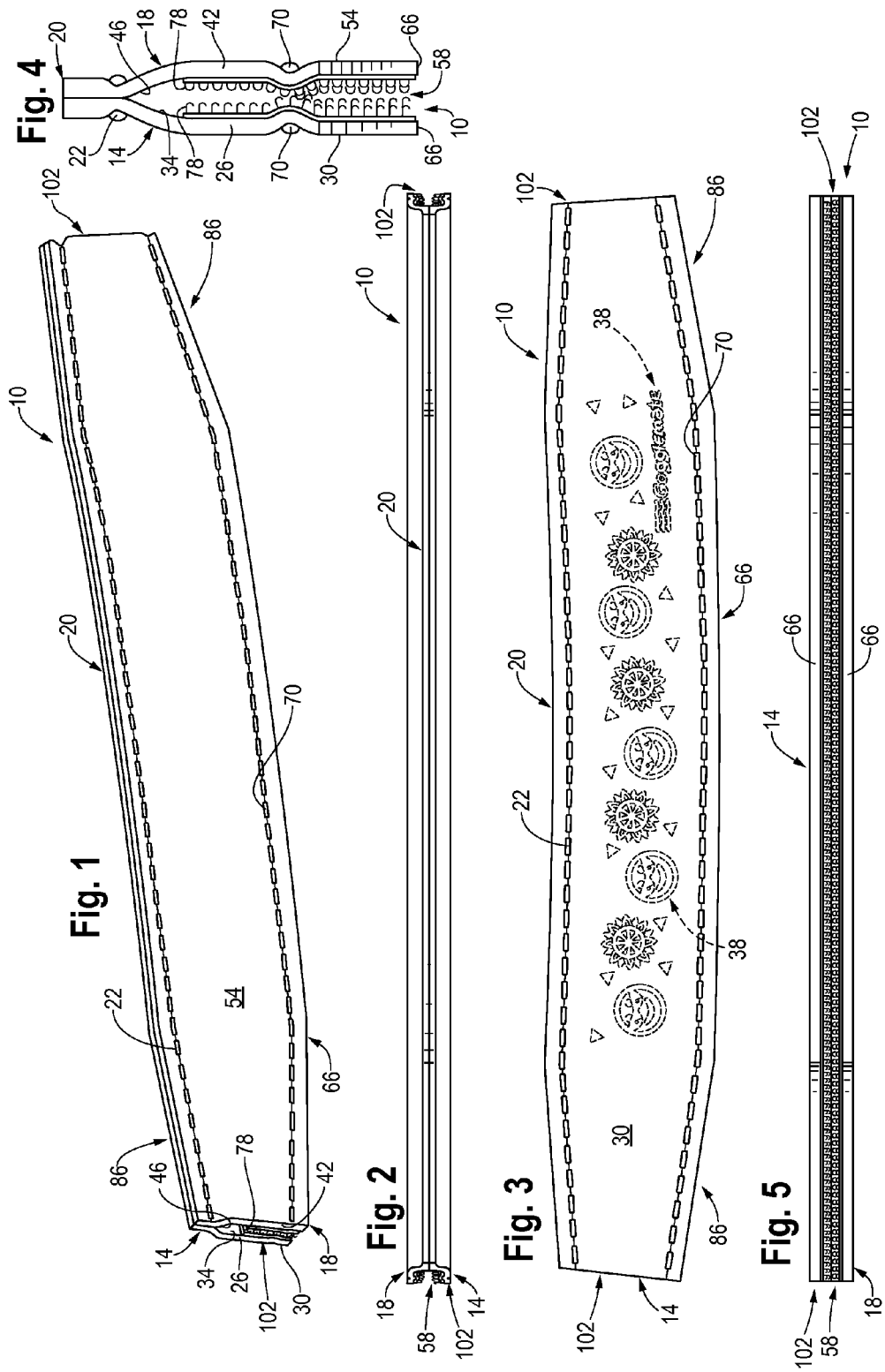

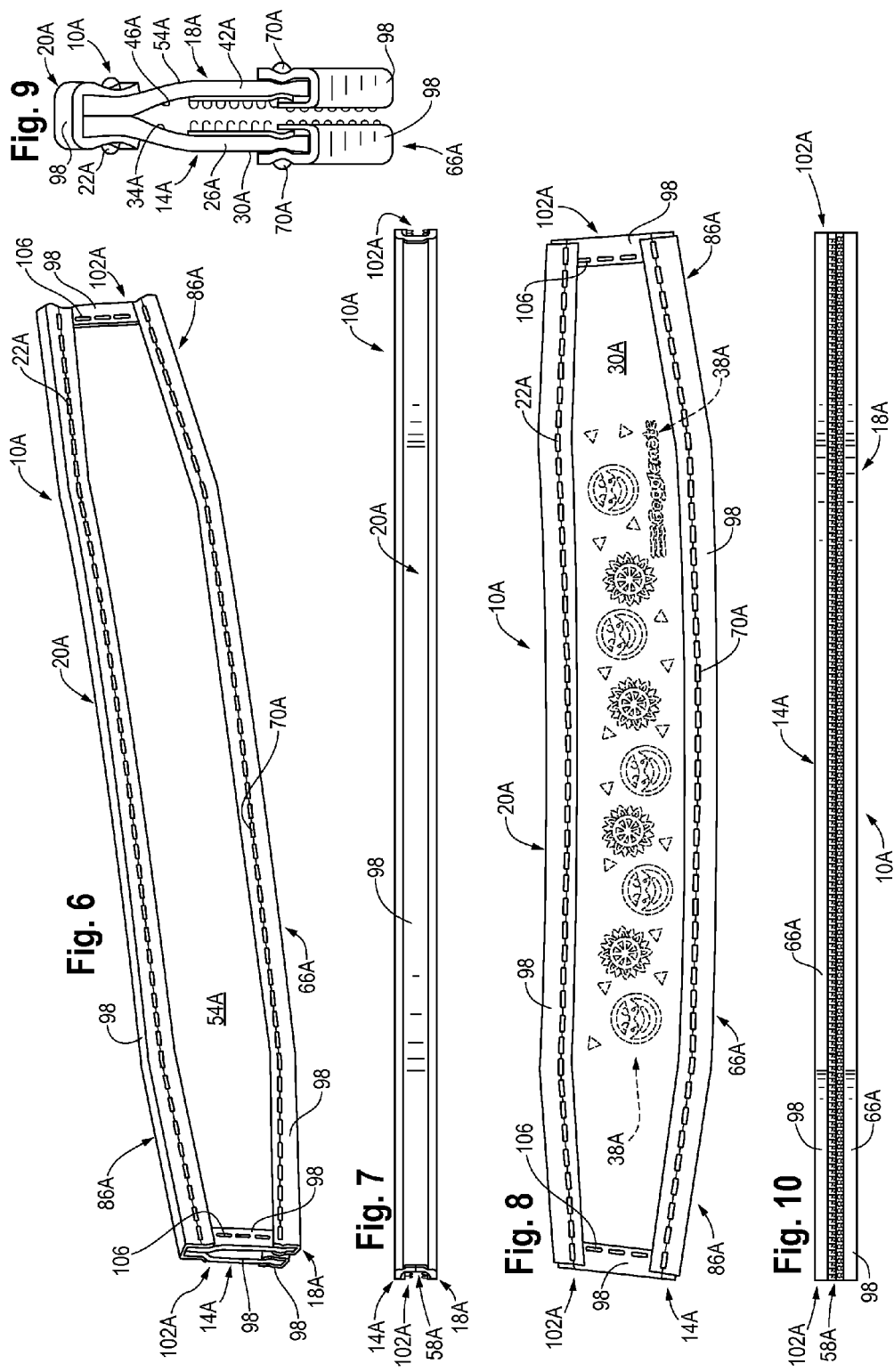

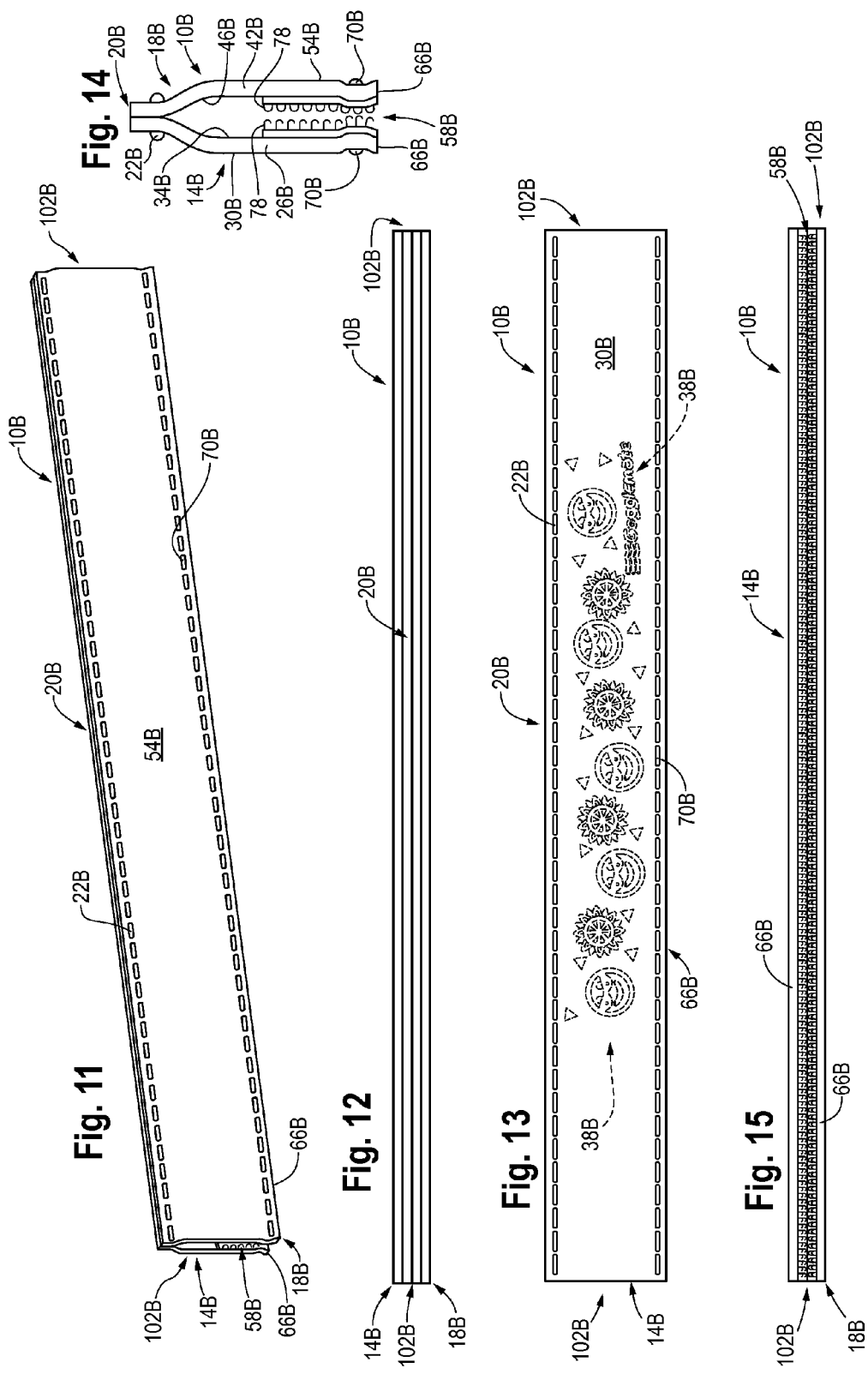

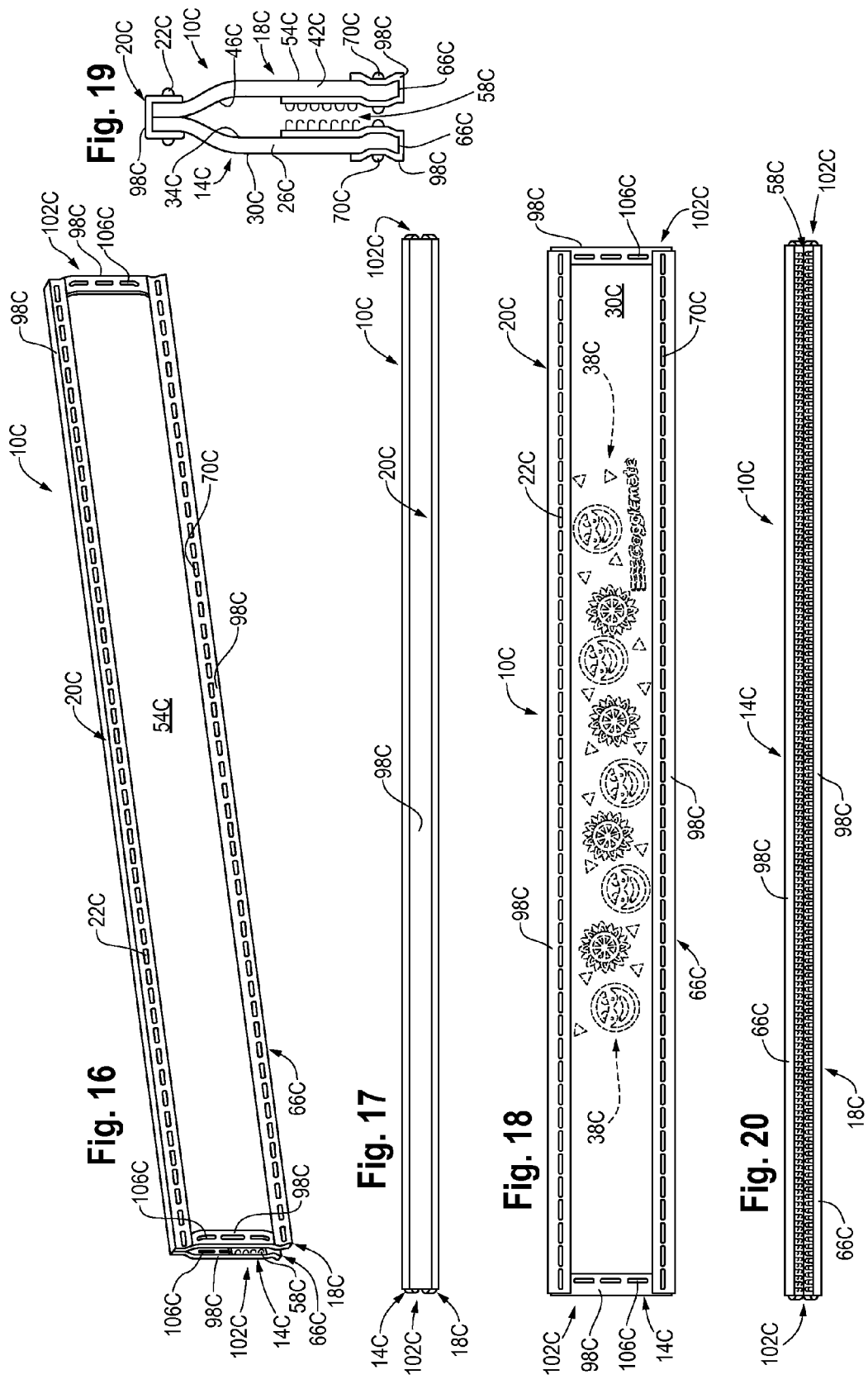

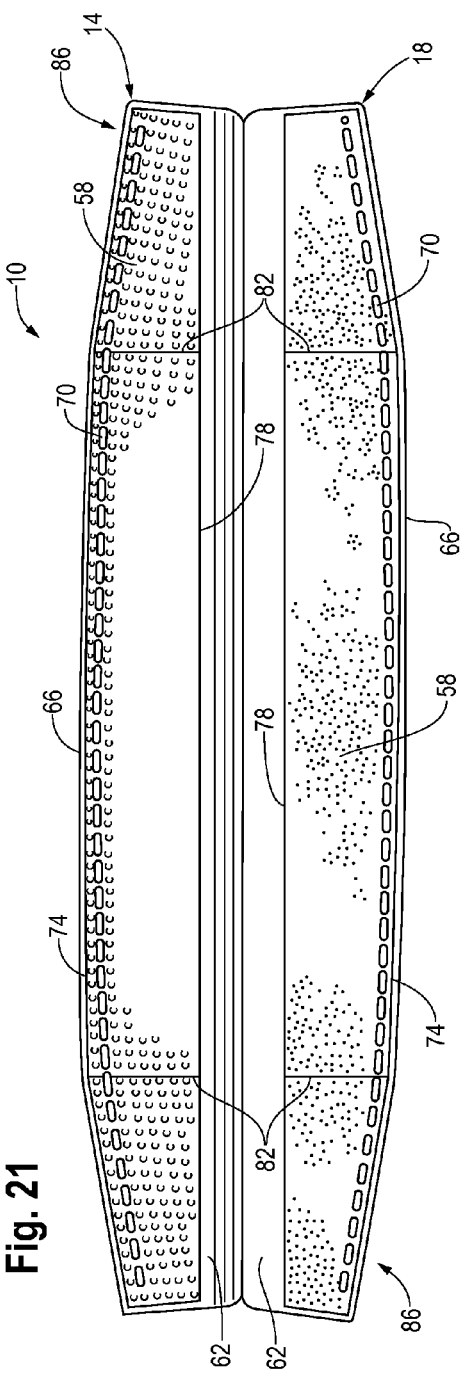
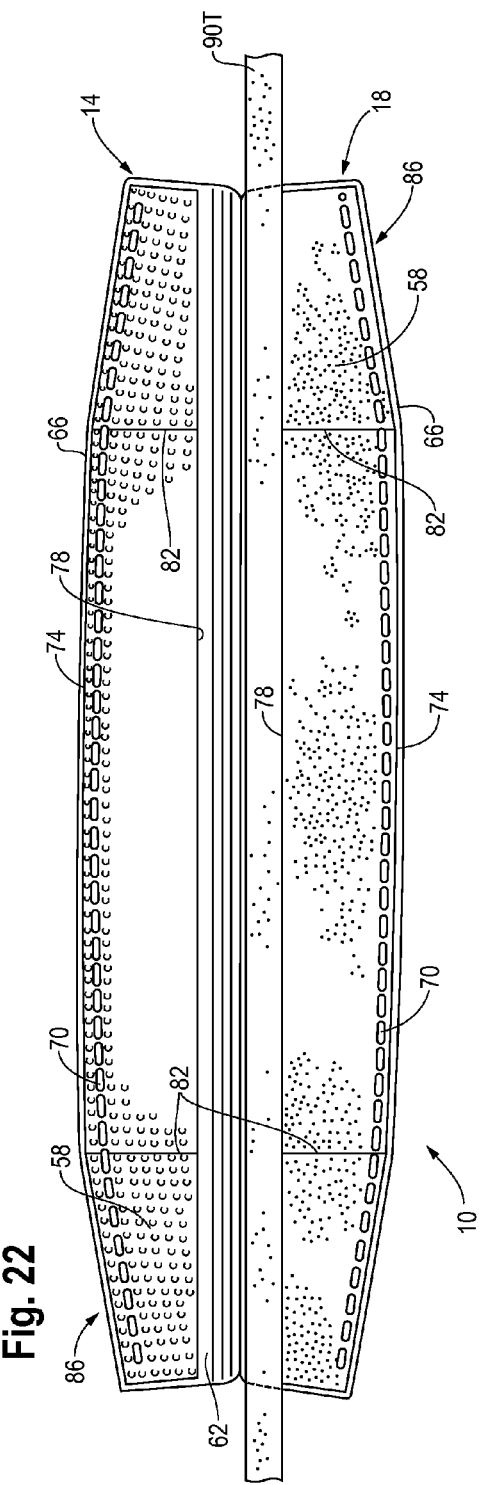
Fig. 21
Fig. 22

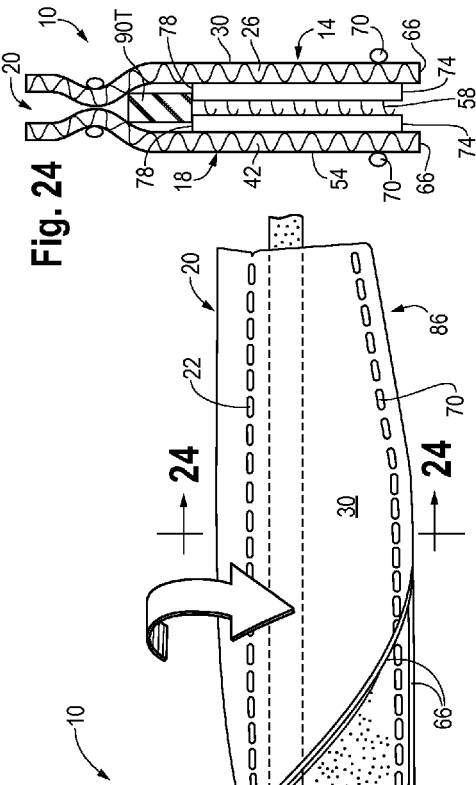
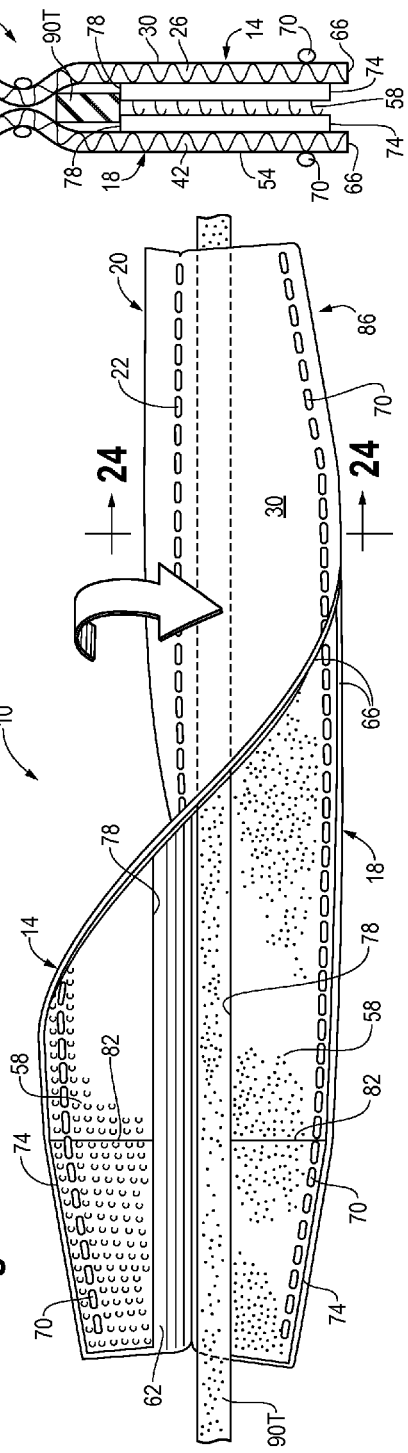
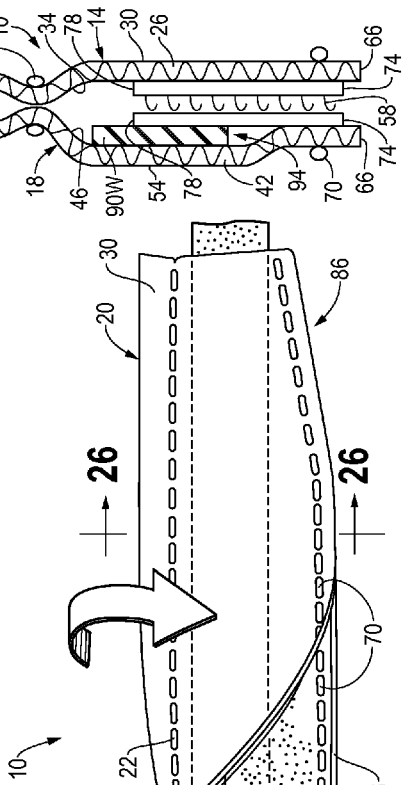
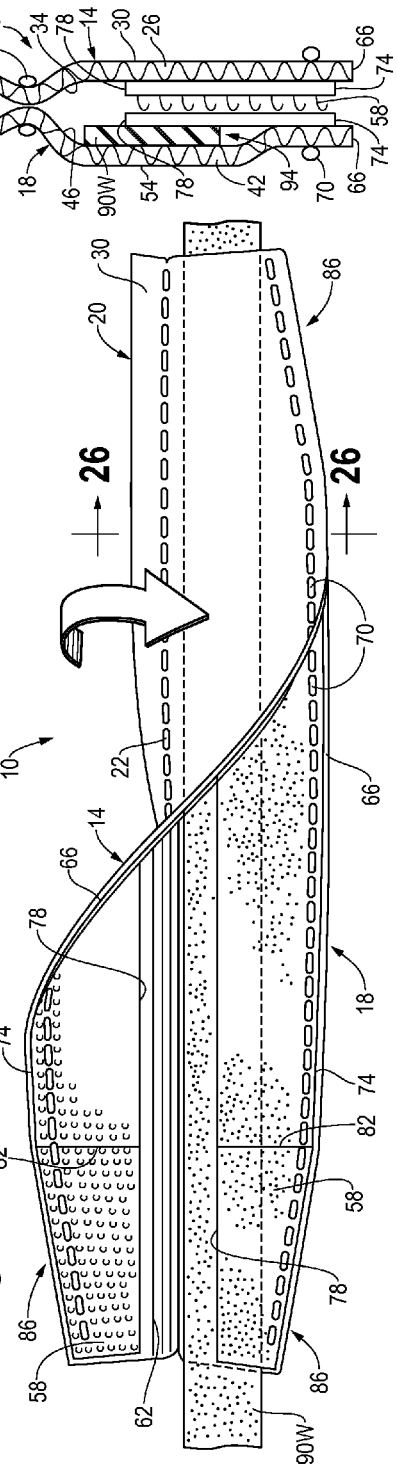

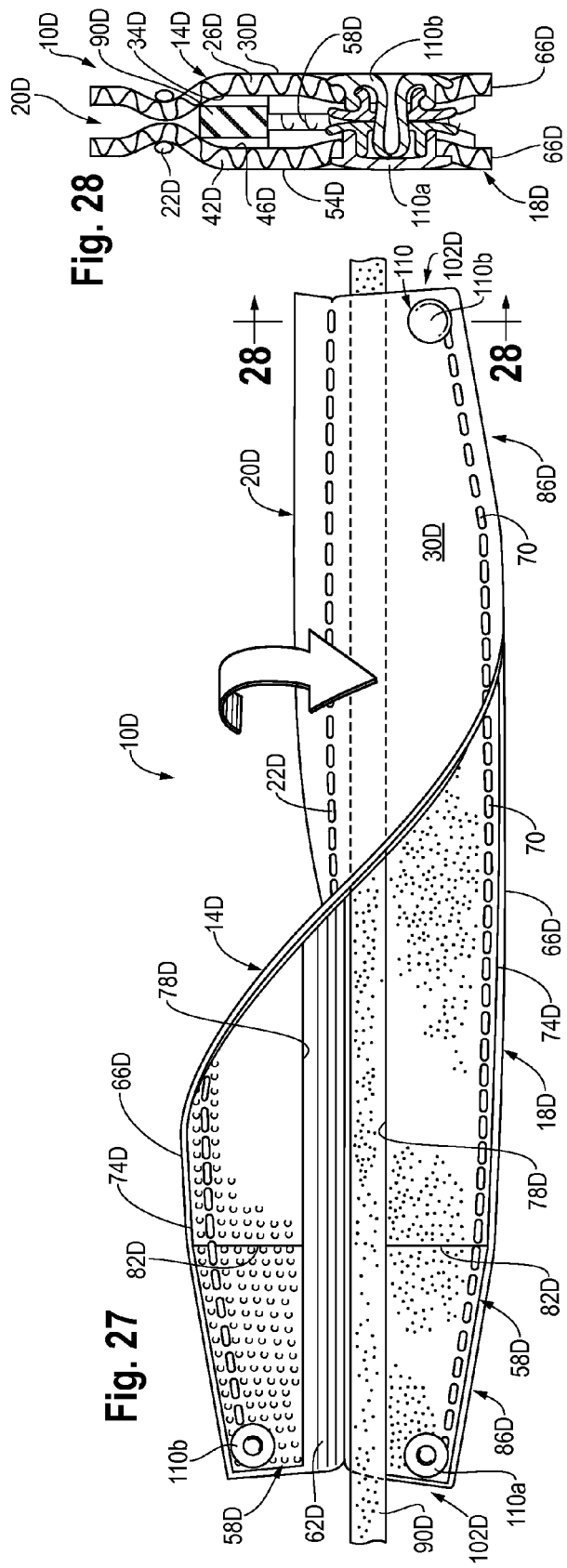

COVER FOR AN EYEWEAR STRAP

RELATED APPLICATIONS

The present application claims the benefit of U.S. Provisional Patent Application No. 61/194,202, filed Sep. 25, 2008, the entire contents of which are incorporated herein by reference.

FIELD OF THE INVENTION

The present invention generally relates to covers for eyewear straps and, more particularly, relates to covers for swim goggle straps that float, provide a variety of decorative indicia, and inhibit the swim goggle straps from tangling with hair.

BACKGROUND

Swim goggles typically include a pair of plastic transparent or translucent cups positionable over a user's eyes and a rubber strap coupled to the plastic cups positionable around a back of a user's head to secure the swim goggles to a user's head. The rubber strap is commonly very thin, extremely flexible, and extremely tight to a user's head, thereby making the strap very difficult to grasp and manipulate when secured around a user's head. Such characteristics of the goggle strap also facilitate tangling of the strap in the user's hair. Once the strap is tangled, removal of the strap from one's hair is a daunting task commonly resulting in yanking the user's hair or even pulling out the user's hair. Also, the swim goggle strap digs or otherwise provides extreme pressure into the back and sides of a user's head, thereby making the swim goggles uncomfortable to wear for long periods of time.

In addition, swim goggles are made of materials that contribute to the goggles sinking in water. Accordingly, swim goggles commonly sink to the bottom of a pool, lake, or other body of water and are lost or at a minimum difficult to find and retrieve. Sinking swim goggles contribute to a high rate of loss

SUMMARY

In some aspects, a cover for an eyewear strap is provided and includes a first member, a second member associated with the first member and movable toward and away from the first member, and a fastener connected to the first member and the second member for removably connecting the first member to the second member, the cover is adapted to receive an eyewear strap between the first and second members when the first and second members are disconnected, and the cover is securable to the eyewear strap when the first and second members are connected together.

In other aspects, a cover for an eyewear strap is provided and includes a first member including a top edge and a bottom edge, a second member including a top edge and a bottom edge, the first and second members are permanently connected together at the top edges thereof, and a fastener connected to the first and second members near the bottom edges thereof for removably connecting the bottom edges of the first and second members, the first and second members are removably connected from each other at the bottom edges thereof while maintaining connection at the top edges of the first and second members.

In further aspects, the first member and the second member may be permanently connected to one another at top edges thereof and may be removably connected to each other at bottom edges thereof.

In yet other aspects, the first and second members may be sewn together at top edges thereof and the fastener may be connected to the first and second members near bottom edges thereof for removably connecting the first and second members together at their bottom edges.

In yet further aspects, the fastener may be a hook and loop type fastener.

In still other aspects, the fastener may be a snap type fastener.

In still further aspects, the fastener may include a first portion connected to the first member and a second portion connected to the second portion, the first and second portions of the fastener may be removably engageable with each other to removably connect the first and second members together.

In other aspects, the first portion of the fastener may include a bottom edge and the second portion of the fastener may include a bottom edge, wherein bottom edges of the first portion and the first member may be oriented near one another and the first portion may be connected to the first member at their bottom edges, and wherein bottom edges of the second portion and the second member may be oriented near one another and the second portion may be connected to the second member at their bottom edges.

In further aspects, top edges of the first and second portions of the fastener may not be connected to the first and second members and may be adapted to move relative to the first and second members.

In yet other aspects, top edges of the first and second portions may be movable away from the first and second members to provide a first gap between the first portion and the first member and a second gap between the second portion and the second member, and wherein bottom edges of the first and second portions and the first and second members may remain connected while the top edges are moved away.

In yet further aspects, an eyewear strap may be positionable in one of the first and second gaps and may be secured to the cover within the one of the first and second gaps when the first and second portions of the fastener are connected together.

In still other aspects, the cover may include a second fastener coupled to the first member and the second member for removably connecting the first member to the second member.

In still further aspects, the fastener may be a hook and loop type fastener and the second fastener may be a snap type fastener.

In other aspects, indicia may be located on at least one of the first and second members.

In further aspects, the indicia may comprise at least one of text and an image.

In yet other aspects, the first and second members may have tapered ends.

In yet further aspects, the first and second members may be unitarily formed as one-piece.

Independent features and independent advantages of the present invention will become apparent to those skilled in the art upon review of the detailed description and drawings.

BRIEF DESCRIPTION OF THE DRAWINGS

FIG. 1 is a rear perspective view of an exemplary cover for eyewear straps, the cover is shown in a closed position;

FIG. 2 is a top view of the cover shown in FIG. 1;

FIG. 3 is a front view of the cover shown in FIG. 1;

FIG. 4 is a left side view of the cover shown in FIG. 1;

FIG. 5 is a bottom view of the cover shown in FIG. 1;

FIG. 6 is a rear perspective view of another exemplary cover for eyewear straps, the cover is shown in a closed position and with a fastener removed;

FIG. 7 is a top view of the cover shown in FIG. 6;

FIG. 8 is a front view of the cover shown in FIG. 6;

FIG. 9 is a left side view of the cover shown in FIG. 6;

FIG. 10 is a bottom view of the cover shown in FIG. 6;

FIG. 11 is a rear perspective view of yet another exemplary cover for eyewear straps, the cover is shown in a closed position;

FIG. 12 is a top view of the cover shown in FIG. 11;

FIG. 13 is a front view of the cover shown in FIG. 11;

FIG. 14 is a left side view of the cover shown in FIG. 11;

FIG. 15 is a bottom view of the cover shown in FIG. 11;

FIG. 16 is a rear perspective view of still another exemplary cover for eyewear straps, the cover is shown in a closed position;

FIG. 17 is a top view of the cover shown in FIG. 16;

FIG. 18 is a front view of the cover shown in FIG. 16;

FIG. 19 is a left side view of the cover shown in FIG. 16;

FIG. 20 is a bottom view of the cover shown in FIG. 16;

FIG. 21 is a front view of the cover shown in FIG. 1, the cover is shown in an open position;

FIG. 22 is a front view similar to FIG. 21 shown with an exemplary eyewear strap disposed in the cover;

FIG. 23 is a front view of the cover shown in FIG. 1 with the cover partially closed upon the exemplary eyewear strap shown in FIG. 22;

FIG. 24 is a cross-sectional view taken along line 24-24 in FIG. 23;

FIG. 25 is a front view of the cover shown in FIG. 1 with the cover partially closed upon another exemplary eyewear strap;

FIG. 26 is a cross-sectional view taken along line 26-26 in FIG. 25;

FIG. 27 is a front view of another exemplary cover for eyewear straps with the cover partially closed upon an exemplary eyewear strap; and FIG. 28 is a cross-sectional view taken along line 28-28 in FIG. 27.

Before any independent features and embodiments of the invention are explained in detail, it is to be understood that the invention is not limited in its application to the details of the construction and the arrangement of the components set forth in the following description or illustrated in the drawings. The invention is capable of other embodiments and of being practiced or of being carried out in various ways. Also, it is understood that the phraseology and terminology used herein is for the purpose of description and should not be regarded as limiting. For example, directional terms such as "top", "bottom", "above", "below", "front", "back", etc. are not intended to be limiting and are used for describing the exemplary illustrated embodiments herein.

DETAILED DESCRIPTION

With reference to FIGS. 1-5, an exemplary cover 10 for an eyewear strap is shown. The exemplary cover 10 may be used with a wide variety of eyewear types such as, for example, swim goggles, athletic safety goggles, racquet ball goggles, sunglasses, etc. While the cover 10 may be used with a wide variety of eyewear types, the following description of the cover 10 will be described in relation to swim goggles. Such following description relating to swim goggles is not intended to be limiting upon the scope of the present invention and is utilized to assist with the understanding of the cover 10.

Swim goggles commonly include a pair of transparent or translucent cups adapted to cover a user's eyes and a strap secured at a first end to one of the cups and secured at a second end to the other of the cups. The strap is adapted to secure the swim goggles to a user's head by extending around sides and a back of the user's head.

The exemplary goggle strap cover 10 includes a first member 14 and a second member 18 formed separately from one another and connected together at top edges 20 of the first and second members 14, 18. In the illustrated exemplary embodiment, the first and second members 14, 18 are connected together by stitching or sewing a thread 22 through the first and second members 14, 18. In other exemplary embodiments, the first and second members 14, 18 may be connected together in other manners such as, for example, heat bonding, snaps, buttons, hook and loop type fasteners, or other manners of connection. In further exemplary embodiments, the first and second members 14, 18 may be unitarily formed as one piece.

In the illustrated exemplary embodiment, the first member 14 includes a core 26, an exterior layer 30 secured to an exterior of the core 26, and an interior layer 34 secured to an interior of the core 26. In some exemplary embodiments, the core 26 may be comprised of NEOPRENE™ and the exterior and interior layers 30, 34 may be comprised of NYLON™. Alternatively, the core 26, the exterior layer 30, and the interior layer 34 may be comprised of materials different than those described above. In other exemplary embodiments, the first member 14 may only include a core 26 and may not include exterior or interior layers. In yet other exemplary embodiments, the first member 14 may include a core 26 and only one of the exterior or interior layers 30 or 34.

When the goggle strap cover 10 is secured to a goggle strap and the goggles are secured to a user's head, the first member 14 will be visible to others. Decorative indicia 38 may be positioned on the exterior layer 30 of the first member 14 or, in embodiments where an exterior layer is not included, the decorative indicia 38 may be positioned on an exterior surface of the core 26. In either embodiment, a variety of different decorative indicia 38 in the form of objects or text may be positioned on the first member 14 including, for example, child-friendly indicia, sports team indicia, customized indicia (i.e., user's name or other wording or images desirable by the user), advertising indicia relating to the goggle strap cover 10 or to a third party entity, etc. Such decorative indicia 38 may be positioned on the first member 14 in a variety of different manners. For example, the decorative indicia 38 may be heat transferred onto the first member 14 with a heat press. In addition, the exterior layer 30 of the first member 14 may be comprised of one or more colors, again providing customization of the goggle strap cover 10.

In the illustrated exemplary embodiment, the second member 18 includes a core 42 and an interior layer 46 secured to an interior surface 50 of the core 42. In some exemplary embodiments, the core 42 may be comprised of NEOPRENE™ and the interior layer 46 may be comprised of NYLON™. In the illustrated exemplary embodiment, the lack of an exterior layer on the second member 18 exposes an exterior surface 54 of the core 42. This exposed exterior surface 54 is the surface of the goggle strap cover 10 that contacts a user's head. Preferably, the exposed exterior surface 54 of the second member 18 is soft to provide comfort and provide friction to inhibit sliding or slipping of the goggle strap cover 10 relative to the user's head. In exemplary embodiments where the core 42 is comprised of NEOPRENE™, the exposed exterior surface 54 of the core 42 may be comprised of raw textured NEOPRENE™, which is often referred to as SHARK-SKIN™.

Alternatively, the core 42 and the interior layer 46 may be comprised of materials different than those described above. In other exemplary embodiments, the second member 18 may only include a core 42 and may not include an interior layer. In yet other exemplary embodiments, the second member 18 may include a core 42, an interior layer 46, and an exterior layer similar to the illustrated exemplary embodiment of the first member 14.

Preferably, the materials chosen to comprise the goggle strap cover 10 ultimately contribute to buoyancy or floatation of the goggle strap cover 10. That is, all of the materials comprising the goggle strap cover 10 may have buoyant properties or a portion of the materials comprising the goggle strap cover 10 may have buoyant properties as long as the buoyant materials account for the weight of the non-buoyant materials to ultimately provide a buoyant goggle strap cover 10.

With continued reference to FIGS. 1-5, the first and second members 14, 18 of the goggle strap cover 10 are permanently secured to each other only near top edges, thereby facilitating opening of the goggle strap cover 10 at its bottom edge. Opening of the cover 10 includes movement of the first and second members 14, 18 away from each other at their bottom edges 66 and rotation about the thread 22 near the top edges of the first and second members 14, 18 to expose an interior of the goggle strap cover 10. Fasteners 58 are connected to interior surfaces 62 of the first and second members 14, 18 near bottom edges 66 of the first and second members 14, 18 to removably secure the bottom edges 66 of the first and second members 14, 18 together. In the illustrated exemplary embodiment, the fasteners 58 are hook and loop type fasteners. The hook portion and loop portion of the hook and loop type fastener 58 may be secured to either of the interior surfaces 62 of the first and second members 14, 18 as long as they are oriented to engage each other to removably secure the bottom edges 66 of the first and second members 14, 18. Also, in the illustrated exemplary embodiment, the hook and loop type fasteners 58 are secured to and near bottom edges 66 of the first and second members 14, 18 by stitching or sewing a thread 70 through each of the first and second members 14, 18. Alternatively, the fasteners 58 may be other types of fasteners such as, for example, a zip fastener (i.e., zipper), buttons, snaps, etc., and may be secured to the first and second members 14, 18 in different manners and in different positions.

With continued reference to FIGS. 1-5 and the illustrated exemplary embodiment of the goggle strap cover 10, the hook and loop type fastener 58 extends substantially the entire length of the goggle strap cover 10 and is secured to the first and second members 14, 18 only near bottom edges 74 of the hook and loop types fasteners 58, thereby leaving top edges 78 of the hook and loop type fasteners 58 unsecured and moveable relative to the interior surfaces 62 of the first and second members 14, 18.

With particular reference to FIG. 21, both the hook portion and loop portion of the hook and loop type fastener 58 are divided into a central portion 58A and ends portions 58B, 58C, one end portion on each side of the central portion. These breaks, slits, or interruptions 82 in the hook and loop type fastener 58 inhibit bunching of the goggle strap cover 10 when secured and in use. Alternatively, the hook and loop type fastener 58 may include more or less interruptions 82 than that illustrated in FIG. 21 and described above.

Referring again to FIGS. 1-5, the goggle strap cover 10 includes tapered ends 86. Such tapering has numerous purposes. For example, the tapered ends 86 of the goggle strap cover 10 are proximate a user's ears when in use and the tapered ends 86 provide less material to contact a user's ears, thereby inhibiting the chance the ends 86 of the goggle strap cover 10 will irritate a user's ears. Also for example, the tapered ends 86 provide less vertical distance between top and bottom edges 20, 66 of the goggle strap cover 10 which provide less vertical distance above and below a goggle strap positioned within the goggle strap cover 10, thereby limiting the strap's vertical movement within the goggle strap cover 10. Substantial vertical movement of the goggle strap may irritate a user's head, allow loosening of the goggle strap, or facilitate tangling of the strap with a user's hair. Further for example, the tapered ends 86 allow the goggle strap cover 10 to lay flatter on a user's head, thereby inhibiting bunching of the goggle strap cover 10.

As indicated above, the goggle strap cover 10 is useable with swim goggles. To position or connect the goggle strap cover 10 to a strap 90 of the swim goggles, the goggle strap cover 10 is first opened by peeling the bottom edges 66 of the goggle strap cover 10 away from each other to unsecure the hook and loop type fastener 58. With the goggle strap cover 10 in the opened position (see FIG. 21), a swim goggles strap 90 may be introduced into the goggle strap cover 10. The width of the swim goggle strap 90 may dictate the manner in which the strap 90 is positioned within the goggle strap cover 10. If the strap 90T is relatively thin in width (see FIG. 22), the strap 90T is positioned within the cover 10 near the top edge 20 of the cover 10. In such instances, the strap 90T may be sufficiently thin to fit above the top edges 78 of the hook and loop portions of the hook and loop type fastener 58 or may slightly overlap the top edges 78 of the hook and loop portions of the hook and loop type fastener 58. In either case, after positioning the relatively thin strap 90T within the cover 10, the first and second members 14, 18 are moved toward each other to secure the hook and loop type fastener 58, thus securing the swim goggle strap 90T within the goggle strap cover 10 (see FIGS. 23 and 24). Conversely, if the swim goggle strap 90W is relatively wide (see FIG. 25), the top edge of one of the hook portion or loop portion of the hook and loop type fastener 58 is moved away from the respective interior surface 62 of the first or second member 14 or 18 to provide a gap 94 (see FIG. 26) between the hook or loop portion and the respective first or second member 14 or 18. The relatively wide strap 90W is then positioned in the gap 94, preferably flat against the interior surface 62 of the respective first or second member 14 or 18, and the one of the hook or loop portion previously moved away is returned toward the respective first or second member 14 or 18 to trap the swim goggle strap 90W. The hook and loop type fastener 58 is then secured together to ultimately secure the swim goggle strap 90W within the goggle strap cover 10 (see FIGS. 25 and 26). It should be understood that a relatively thin goggle strap 90T may also be secured within the goggle strap cover 10 in the same manner as the relatively wide strap 90W described above.

Upon securing the goggle strap cover 10 to the swim goggle strap 90, a user may appropriately place the swim goggles and the goggle strap cover 10 on their head. The goggle strap cover 10 is preferably positioned at the back of the user's head with the tapered ends 86 wrapping around sides of the user's head and the exterior surface 54 of the second member 18 engaging the user's head. The goggle strap cover 10 is removed from the swim goggle strap 90 by reversing the securing steps described above.

Referring now to FIGS. 6-10, another exemplary goggle strap cover 10A is illustrated. Common elements between the exemplary goggle strap cover 10A of FIGS. 6-10 and the exemplary goggle strap cover 10 of FIGS. 1-5 and 21-26 are identified by the same reference numbers and an "A".

The exemplary goggle strap cover 10A includes a plurality of edge members 98 covering edges of the goggle strap cover 10A. The edge members 98 are positioned over exposed edges of the goggle strap cover 10A to protect or conceal the edges of the first and second members 14A, 18A, which may be, in some embodiments, a rough cut edge or otherwise aesthetically unpleasing. The edge members 98 provide a smooth, congruent edge and may be colored or decorated with indicia to provide a desirable appearance. Also, the edge members 98 may protect the exposed edge of the first and second members 14A, 18A from fraying or otherwise deteriorating. The edge members 98 cover top edges 20A of the first and second members 14A, 18A, bottom edges 66A of the first and second members 14A, 18A, and end edges 102 of the first and second members 14A, 18A. Accordingly, every edge of the goggle strap cover 10A is covered by an edge member 98. In other exemplary embodiments, less than all of the edges of the goggle strap cover 10A may be covered. In the illustrated exemplary embodiment, the edge members 98 covering the top and bottom edges 20A, 66A of the first and second members 14A, 18A are connected to the first and second members 14A, 18A by the same thread 22A used to connect the top edges 20A of the first and second members 14A, 18A and the same thread 70A to connect the hook and loop type fastener 58A to the first and second members 14A, 18A. In other exemplary embodiments, the edge members 98 covering the top and bottom edges 20A, 66A of the first and second members 14A, 18A may be connected in other manners such as, for example, heat bonding, snaps, buttons, hook and loop type fasteners, or other manners of connection. In the illustrated exemplary embodiment, the edge members 98 covering the end edges 102 of the first and second members 14A, 18A are connected to the first and second members 14A, 18A by stitching or sewing a thread 106 through the edge members 98 and the first and second members 14A, 18A. In other exemplary embodiments, the edge members 98 covering end edges 102 of the first and second members 14A, 18A may be connected to the first and second members 14A, 18A in other manners such as, for example, heat bonding, snaps, buttons, hook and loop type fasteners, or other manners of connection.

Referring now to FIGS. 11-15, another exemplary goggle strap cover 10B is illustrated. Common elements between the goggle strap cover 10B of FIGS. 11-15 and the exemplary goggle strap covers 10, 10A of FIGS. 1-5 and 21-26, and FIGS. 6-10 are identified by the same reference numbers and a "B".

This exemplary goggle strap cover 10B includes first and second members 14B, 18B that are substantially rectangular in shape, thereby providing a rectangular shaped goggle strap cover 10B. This embodiment of the goggle strap cover 10B does not include tapered ends like those included in the goggle strap covers 10, 10A illustrated in FIGS. 1-5 and 21-26, and FIGS. 6-10.

Referring now to FIGS. 16-20, another exemplary goggle strap cover 10C is illustrated. Common elements between the goggle strap cover 10C of FIGS. 16-20 and the exemplary goggle strap covers 10, 10A, 10B of FIGS. 1-5 and 21-26, FIGS. 6-10, and FIGS. 11-15 are identified by the same reference numbers and a "C".

This exemplary goggle strap cover 10C includes a plurality of edge members 98C covering edges 20C, 66C, 102C of the goggle strap cover 10C. The edge members 98C are positioned over exposed edges 20C, 66C, 102C of the goggle strap cover 10C to protect or conceal the edges of the first and second members 14C, 18C, which may be, in some embodiments, a rough cut edge or otherwise be aesthetically unpleasing. The edge members 98C provide a smooth, congruent edge and may be colored or decorated with indicia to provide a desirable appearance. Also, the edge members 98C may protect the exposed edge 20C, 66C, 102C of the first and second members 14C, 18C from fraying or otherwise deteriorating. The edge members 98C cover top edges 22C of the first and second members 14C, 18C, bottom edges 66C of the first and second members 14C, 18C, and end edges 102C of the first and second members 14C, 18C. Accordingly, every edge of the goggle strap cover 10C is covered by an edge member 98C. In other exemplary embodiments, less than all of the edges of the goggle strap cover 10C may be covered. In the illustrated exemplary embodiment, the edge members 98C covering the top and bottom edges 20C, 66C of the first and second members 14C, 18C are connected to the first and second members 14C, 18C by the same thread 22C used to connect the top edges 20C of the first and second members 14C, 18C and the same thread 70C to connect the hook and loop type fastener 58C to the first and second members 14C, 18C. In other exemplary embodiments, the edge members 98C covering the top and bottom edges 20C, 66C of the first and second members 14C, 18C may be connected in other manners such as, for example, heat bonding, snaps, buttons, hook and loop type fasteners, or other manners of connection. In the illustrated exemplary embodiment, the edge members 98C covering the end edges 102C of the first and second members 14C, 18C are connected to the first and second members 14C, 18C by stitching or sewing a thread 106C through the edge members 98C and the first and second members 14C, 18C. In other exemplary embodiments, the edge members 98C covering end edges 102C of the first and second members 14C, 18C may be connected to the first and second members 14C, 18C in other manners such as, for example, heat bonding, snaps, buttons, hook and loop type fasteners, or other manners of connection.

Referring now to FIGS. 27 and 28, yet another exemplary goggle strap cover 10D is illustrated. Common elements between the goggle strap cover 10D of FIGS. 27 and 28 and the exemplary goggle strap covers 10, 10A, 10B, 10C of FIGS. 1-5 and 21-26, FIGS. 6-10, FIGS. 11-15, and FIGS. 16-20 are identified by the same reference numbers and a "D".

This exemplary goggle strap cover 10D includes a second set of fasteners 110 for securing the first and second members 14D, 18D together. In the illustrated exemplary embodiment, the second set of fasteners are snaps 110. In other exemplary embodiments, the second set of fasteners 110 may be other types of fasteners including, for example, hook and loop type fasteners, buttons, a zip fastener (i.e., zipper), etc. Returning to the illustrated exemplary embodiment, the snaps 110 are positioned near bottom corners of the goggle strap cover 10D and removably connect to provide additional securement between the first and second members 14D, 18D. Each snap 110 comprises two components, one receptacle component 110a and one projection component 110b, removably engageable with each other to secure the snap 110. One of the receptacle and projection components 110a, 110b is secured to the first member 14D and the other of the receptacle and projection components 110a, 110b is secured to the second member 18D. When the cover 10D is in the open position (see left portion of FIG. 27), the two components 110a, 110b are unsecured and displaced from one another. When the cover 10D is in the closed position (see right portion of FIG. 27), the two components 110a, 110b engage and secure together to provide additional securement of the cover 10D in the closed position. Similar to the other exemplary embodiments of the cover, a goggle strap 90D may be secured within the goggle strap cover 10D. In this exemplary embodiment, the strap 90D is disposed between the snaps 110 and the thread 22D used to secure the top edges 20D of the first and second members 14D, 18D. Alternatively, the strap 90D may be disposed in the gap 94D between the fastener 58D and one of the first or second members 14D, 18D and still be positioned between the snaps 110 and the thread 22D used to secure the top edges 20D of the first and second members 14D, 18D.

The foregoing description has been presented for purposes of illustration and description, and is not intended to be exhaustive or to limit the invention to the precise form disclosed. The descriptions were selected to explain the principles of the invention and their practical application to enable others skilled in the art to utilize the invention in various embodiments and various modifications as are suited to the particular use contemplated. Although particular constructions of the present invention have been shown and described, other alternative constructions will be apparent to those skilled in the art and are within the intended scope of the present invention.

I claim:

1. A cover for an eyewear strap, the cover comprising:
   a first member;
   a second member associated with the first member and movable toward and away from the first member; and
   a fastener connected to the first member and the second member for removably connecting the first member to the second member;
   wherein the cover is adapted to receive an eyewear strap between the first and second members when the first and second members are disconnected, and wherein the cover is securable to the eyewear strap when the first and second members are connected together;
   wherein the fastener includes a first portion connected to the first member and a second portion connected to the second member, the first and second portions of the fastener are removably engageable with each other to removably connect the first and second members together;
   wherein the first portion of the fastener includes a bottom edge and the second portion of the fastener includes a bottom edge, wherein bottom edges of the first portion and the first member are oriented near one another and the first portion is connected to the first member at their bottom edges, and wherein bottom edges of the second portion and the second member are oriented near one another and the second portion is connected to the second member at their bottom edges;
   wherein top edges of the first and second portions of the fastener are not connected to the first and second members and are adapted to move relative to the first and second members; and
   wherein top edges of the first and second portions are movable away from the first and second members to provide a first gap between the first portion and the first member and a second gap between the second portion and the second member, and wherein bottom edges of the first and second portions and the first and second members remain connected while the top edges are moved away.

2. The cover of claim 1, wherein the first member and the second member are permanently connected to one another at top edges thereof and removably connected to each other at bottom edges thereof.

3. The cover of claim 2, wherein the first and second members are sewn together at top edges thereof and the fastener is connected to the first and second members near bottom edges thereof for removably connecting the first and second members together at their bottom edges.

4. The cover of claim 3, wherein the fastener is a hook and loop type fastener.

5. The cover of claim 3, wherein the fastener is a snap type fastener.

6. The cover of claim 1, wherein the eyewear strap is positionable in one of the first and second gaps and is secured to the cover within the one of the first and second gaps when the first and second portions of the fastener are connected together.

7. The cover of claim 1, wherein the cover includes a second fastener connected to the first member and the second member for removably connecting the first member to the second member.

8. The cover of claim 7, wherein the fastener is a hook and loop type fastener and the second fastener is a snap type fastener.

9. The cover of claim 1, further comprising indicia located on at least one of the first and second members.

10. The cover of claim 9, wherein the indicia comprises at least one of text and an image.

11. The cover of claim 1, wherein the first and second members have tapered ends.

12. The cover of claim 1, wherein the first and second members are unitarily formed as one-piece.

13. A cover for an eyewear strap, the cover comprising:
    a first member including a top edge and a bottom edge;
    a second member including a top edge and a bottom edge, the first and second members are permanently connected together at the top edges thereof; and
    a fastener connected to the first and second members near the bottom edges thereof for removably connecting the bottom edges of the first and second members;
    wherein the first and second members are removably connected from each other at the bottom edges thereof while maintaining connection at the top edges of the first and second members;
    wherein the fastener includes a first portion connected to the first member and a second portion connected to the second portion, the first and second portions of the fastener are removably engageable with each other to removably connect the first and second members together;
    wherein the first portion of the fastener includes a bottom edge and the second portion of the fastener includes a bottom edge, wherein bottom edges of the first portion and the first member are oriented near one another and the first portion is connected to the first member at their bottom edges, and wherein bottom edges of the second portion and the second member are oriented near one another and the second portion is connected to the second member at their bottom edges;
    wherein top edges of the first and second portions of the fastener are not connected to the first and second members and are adapted to move relative to the first and second members; and
    wherein top edges of the first and second portions are movable away from the first and second members to provide a first gap between the first portion and the first member and a second gap between the second portion and the second member, and wherein bottom edges of the first and second portions and the first and second members remain connected while the top edges are moved away.

14. The cover of claim 13, wherein the first and second members are sewn together at top edges thereof.

15. The cover of claim 13, wherein the fastener is a hook and loop type fastener.

16. The cover of claim 13, wherein the fastener is a snap type fastener.

17. The cover of claim 13, wherein an eyewear strap is positionable in one of the first and second gaps and is secured to the cover within the one of the first and second gaps when the first and second portions of the fastener are connected together.

18. The cover of claim 13, wherein the cover includes a second fastener connected to the first member and the second member for removably connecting the first member to the second member.

19. The cover of claim 18, wherein the fastener is a hook and loop type fastener and the second fastener is a snap type fastener.

20. The cover of claim 13, further comprising indicia located on at least one of the first and second members.

21. The cover of claim 20, wherein the indicia comprises at least one of text and an image.

22. The cover of claim 13, wherein the first and second members have tapered ends.

* * * * *